United States Patent
Khouri

(10) Patent No.: US 9,179,986 B2
(45) Date of Patent: Nov. 10, 2015

(54) ORTHODONTIC PLIERS FOR FOUR QUADRANT V-BENDS

(71) Applicant: Suhail A. Khouri, Ballwin, MO (US)

(72) Inventor: Suhail A. Khouri, Ballwin, MO (US)

(*) Notice: Subject to any disclaimer, the term of this patent is extended or adjusted under 35 U.S.C. 154(b) by 74 days.

(21) Appl. No.: 13/657,266

(22) Filed: Oct. 22, 2012

(65) Prior Publication Data
US 2013/0183631 A1 Jul. 18, 2013

Related U.S. Application Data

(60) Provisional application No. 61/632,129, filed on Jan. 18, 2012.

(51) Int. Cl.
*A61C 7/04* (2006.01)
*A61C 7/02* (2006.01)
*B25B 7/00* (2006.01)

(52) U.S. Cl.
CPC . *A61C 7/04* (2013.01); *A61C 7/026* (2013.01); *B25B 7/00* (2013.01)

(58) Field of Classification Search
CPC ............ A61C 7/04; A61C 7/026; A61C 7/02; B21F 3/00; B21F 1/06; B25B 7/00; B25B 7/02
USPC ............ 433/4, 7, 24; 606/205, 206, 207, 210; 140/102, 102.5, 104, 123, 149; 81/303, 81/304, 307, 308, 309, 310, 418, 420, 81/426.5

See application file for complete search history.

(56) References Cited

U.S. PATENT DOCUMENTS

| | | | | |
|---|---|---|---|---|
| 131,188 | A * | 9/1872 | Sneider | 86/40 |
| 715,674 | A | 12/1902 | Lemon | 81/426 |
| 1,171,221 | A * | 2/1916 | Marion | 7/128 |
| 2,824,583 | A * | 2/1958 | Knoester | 140/104 |
| 2,954,606 | A | 10/1960 | Peak | 433/4 |
| 3,041,729 | A | 7/1962 | Tofflemire | 433/159 |
| 3,130,616 | A * | 4/1964 | Miller | 30/91.2 |
| 3,804,132 | A | 4/1974 | Mann | 433/4 X |
| 4,073,179 | A | 2/1978 | Hickey et al. | 81/426 X |
| 4,081,909 | A | 4/1978 | Garcia | 433/4 |
| 5,395,236 | A * | 3/1995 | Khouri | 433/4 |
| 7,032,627 | B1 * | 4/2006 | Sheriff | 140/102.5 |
| 7,182,595 | B2 * | 2/2007 | Smith et al. | 433/4 |
| 7,343,939 | B1 * | 3/2008 | Sheriff | 140/102.5 |
| 7,717,017 | B2 * | 5/2010 | McBride et al. | 81/342 |
| 2002/0146665 | A1 * | 10/2002 | Tamura | 433/159 |
| 2008/0274435 | A1 * | 11/2008 | Wool | 433/4 |

* cited by examiner

*Primary Examiner* — Robyn Doan
*Assistant Examiner* — Tatiana Nobrega

(57) ABSTRACT

A single pair of pliers for bending orthodontic arch wires in all quadrants of a patient's mouth. Includes first and second actuating members, each including a handle portion for grasping in the hand, and a head portion that projects at an angle. The actuating members are pivotally joined so that the head portions can be moved toward and away from each other into respective closed and open positions. A first occlusal jaw on head portion of the first actuating member has an internally angled channel profile and a second occlusal jaw on the head portion of the second actuating member also has an internally angled channel profile facing the other internal channel. A gingival jaw member having upper and lower externally angled corners is adapted to mate with the internally angled profiles of the upper and lower occlusal jaws, respectively, when the head portions are in the closed position.

3 Claims, 9 Drawing Sheets

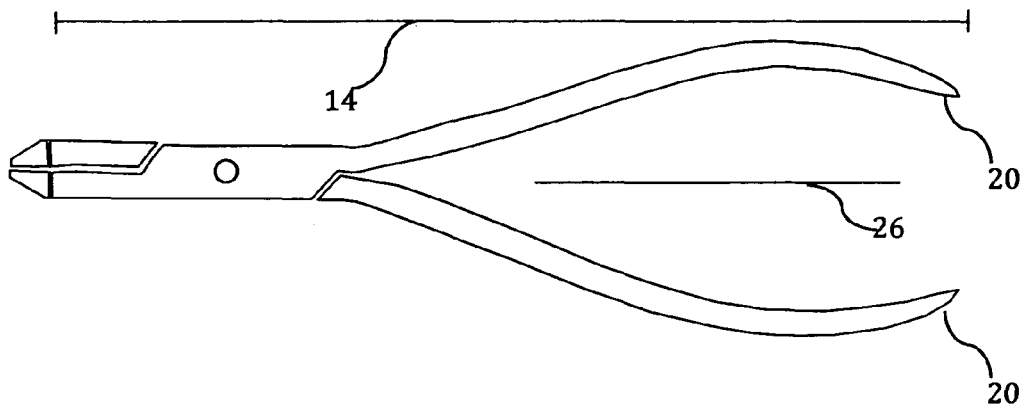
Figure 2. A, over all back view of the pliers
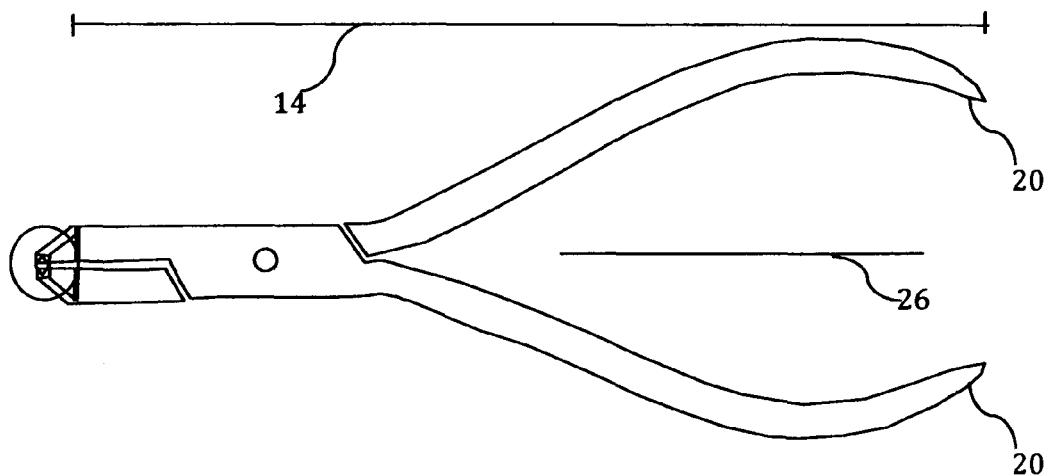
Figure 2 B. Overall front view of the pliers

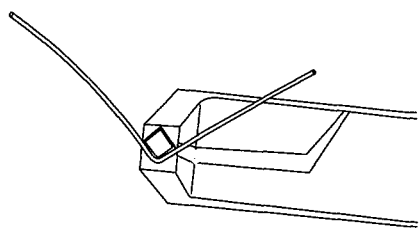
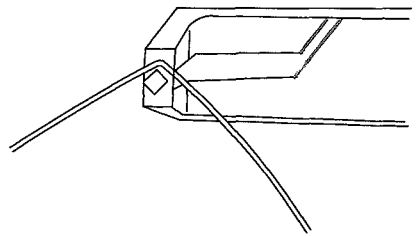
FIG. 8A     FIG. 8B
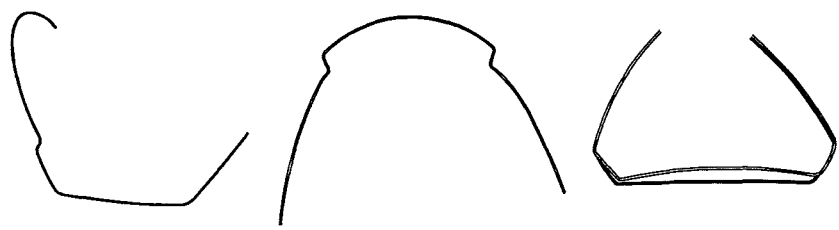
FIG.9A     FIG. 9B     FIG.9C

ORTHODONTIC PLIERS FOR FOUR QUADRANT V-BENDS

RELATED APPLICATION

This application claims priority under 35 U.S.C. §119(e) from U.S. Provisional App. No. 61/632,129 filed Jan. 18, 2012 for "Orthodontic Pliers for Four Quadrant V-Bends".

BACKGROUND

In the practice of orthodontics, super elastic arch wires are secured to misaligned teeth for applying directional forces such that the teeth can be realigned. To bend and activate super elastic arch wires in four quadrants of a patient's mouth, two pairs of specialized pliers were needed, i.e., left hand and right hand pliers. These are commercially available as Bendistal Pliers, and are based on the description in my U.S. Pat. No. 5,395,236 issued Mar. 7, 1995 for "Orthodontic Pliers".

SUMMARY

The single pair of pliers disclosed herein is designed to combine all functions of both left and right conventional pliers.

This one pair of orthodontic pliers is intended to place a permanent V-bend on all kinds and sizes of super elastic wires, extra orally and intraorally, in all quadrants of a patient's mouth.

In general, the disclosure for the present invention is directed to a pair of orthodontic pliers for bending dental arch wires, comprising: (a) first and second elongated actuating members, each actuating member including a handle portion for grasping in the hand, and a head portion, the actuating members being pivotally joined so that the head portions can be moved toward and away from each other into respective closed and open positions; (b) a first, upper occlusal jaw at or in the head portion of the first actuating member, and having an internally angled profile; (c) a second, lower occlusal jaw at or in the head portion of the second actuating member, and having an internally angled profile facing the internal profile of the upper occlusal jaw; and (d) a gingival jaw member having upper and lower externally angled profiles adapted to mate with the internally angled profiles of the upper and lower occlusal jaws, respectively, when the head portions are in the closed position.

Preferably, the gingival jaw member is on an arm that is pivotally mounted on the handle or head for free movement toward and away from either of the occlusal jaw members during positioning of the jaws against the wire.

Another aspect of the disclosure is a method of making a permanent bend on all kinds and sizes of super elastic wires, extra orally and intraorally, in all quadrants of patient's mouth, using one and the same orthodontic pliers.

Orthodontists can access arch wires from right buccal sulcus to place an intrusive V-bend on tied arch wire in the upper right quadrant of a patient's mouth, by placing the wire between the lower occlusal and gingival jaw and squeezing the handle of the pliers. For making an intrusive bend on wire in the lower right quadrant, the orthodontist can place the wire between the upper occlusal jaw and the gingival jaw before squeezing. With some pliers, the orthodontist can then invert the positions in the left side quadrants. For making an intrusive V-bend in the upper left quadrant, the orthodontist can place the wire between the lower occlusal jaw and gingival jaw, before squeezing fully. For making an intrusive V-bend on lower arch wire in the lower left quadrant, the orthodontist can place the wire between the upper occlusal jaw and gingival jaw, before squeezing fully.

The pliers preferably have the bending jaws at an obtuse angle with the long axis of at least about 110 degrees, whereas this angle in the prior art is 90 degrees. The reason for this improvement is to gain easier access for intraorally bending of the back segments of tied wire, as well as being more convenient for orthodontists to use in patient's narrow buccal sulci.

The internal profiles of the occlusal jaw members are elongated a form a trench-like channel having two converging sides. Each side of each channel has an equal width for more control when bending.

The angle formed by the two side surfaces of each occlusal jaw channel is preferably 80 degrees instead of an obtuse angle. This improvement provides a permanent bend that is about 95-100 degrees, which does not fade away upon deactivation. This particular change contributes to creating a light and consistent force level that stays active for longer time, over a longer range of wire activation. This preferred aspect of the pliers is especially noteworthy.

The externally wedge shaped, elongated gingival jaw corners that engage snugly along the full length of the internally angled channels of the occlusal jaws of the new pliers also form an angle of about 80 degrees to insure perfect fitting and consequently making a much more lasting active bend of the wire, which is one ultimate objective of this improvement.

The two surfaces of the occlusal jaw channel meet in a fairly sharp line angle. This design improvement, along with the sharp line of the gingival jaw wedge that fits perfectly with that channel, creates sharpness in the V-bend that gives arch wire the consistency in force delivery of super elastic wires. Also, the resulting sharp and permanent bend is an optimal one, since the pliers bend super elastic wires before they reach the fatigue or breaking point.

Such improvement in so many aspects renders the present invention not only very effective clinically, but convenient to use for patients and orthodontists as well.

BRIEF DESCRIPTION OF THE DRAWING

Aspects of the invention will be described in greater detail below, with reference to the accompanying drawing, in which:

FIGS. 2A and 2B are schematic back and front views of the pliers of FIG. 1;

FIGS. 8A and 8B are schematics showing the same pair of pliers as shown in FIG. 7, for making opposing V-bends on upper and lower arch wires in the upper and lower quadrants of the left side;

FIGS. 9A-9C show examples of permanent activation bends that can be placed on super elastic titanium and nickel titanium wires extra-orally and intra-orally.

DETAILED DESCRIPTION

Figure 1:
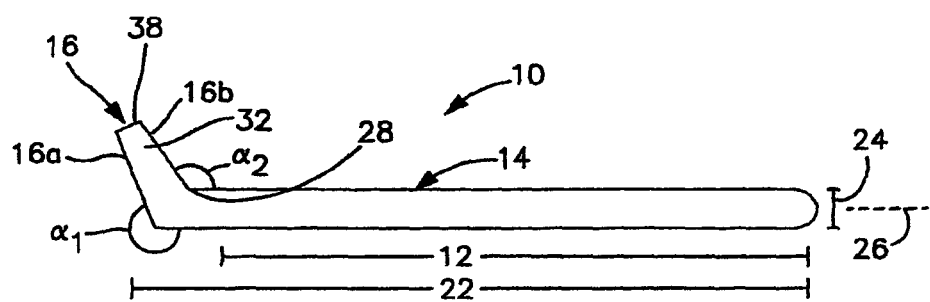
FIG. 1 is a schematic left side view the pliers.

FIG. 1 is a side view of a generalized schematic of the inventive pliers 10, and FIGS. 2A and 2B show the back and front view of the pliers.

As is typical, the pliers 10 has first and second elongated actuating members, each actuating member including a handle portion 14 for grasping in the hand, and a head portion 16, with the actuating members being pivotally joined at 34 so that the head portions can be moved toward and away from each other into respective closed and open positions. When in the closed position, the two substantially symmetric heads can be considered as forming a composite head.

The outer side 16a of the head 16 is preferably 13 mm and makes a 120 degree angle $\alpha_1$ with the long axis 26 of the pliers, while the length of inner side 16b of the head is preferably 10 mm and makes a 135 degree angle $\alpha_2$ with the long axis. This gives the head a slightly tapered shape 32 viewed from the side, as it projects from the base line 28 of the body portion 18, thereby reducing the head side thickness from 7 mm at the base, to 4 mm at the tip 38 of the head.

The overall shape and measurements are preferably similar to the Bendistal Pliers, e.g., a length 22 of 13.5 cm, a side thickness of 7 mm of each leg 24 of handle 14, a 5.5 cm width span of the legs 20 of the handle portion, and a 10 mm width of the body 18. The pivot 34 in the body 18 is shown as a box joint. The length of the body 18 from the point where the legs 20 meet on closure, and the very tip 38 of the pliers, is 5 cm. Each of the two head portions also preferably has an inner taper 30 with the width of the overall head reducing from about 10 mm at the base line 28 to about 4 mm at the tip 38.

Figure 3:
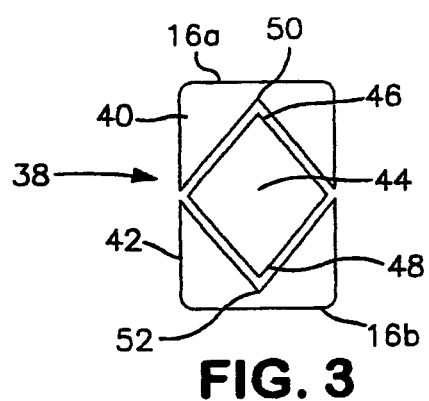
FIG. 3 is a cross section of the tip or nose of the head, showing the double angled rhomboidally shaped gingival jaw between opposed occlusal jaws.

FIG. 3 is a cross section of the tip 38 or nose of the head 16, showing the central, gingival jaw member 44, which has the shape of a rhombus with the upper and lower bending corners 46, 48 having angles of 80 degrees. The angles of the other, non-bending corners of the rhombus are each 100 degrees. The angles of each generally V-shaped channels 50, 52 of the occlusal jaws 40, 42 are similarly 80 degrees in order to conform and fit close to or snugly with the bending corners 46, 48 of the gingival jaw 44.

The active tip 38 thus includes three main components: first and second occlusal jaws 40, 42 that are similar and opposing each other and a central (double gingival) jaw 44 located between them. These can be described as defining a first, upper occlusal jaw at or in the head portion of the first actuating member, having an internally angled profile; a second, lower occlusal jaw at or in the head portion of the second actuating member, having an internally angled profile facing the internal profile of the upper occlusal jaw; and a gingival jaw member having upper and lower externally angled profiles adapted to mate with the internally angled profiles of the upper and lower occlusal jaws, respectively, when the head portions are in the closed position.

Figure 4:
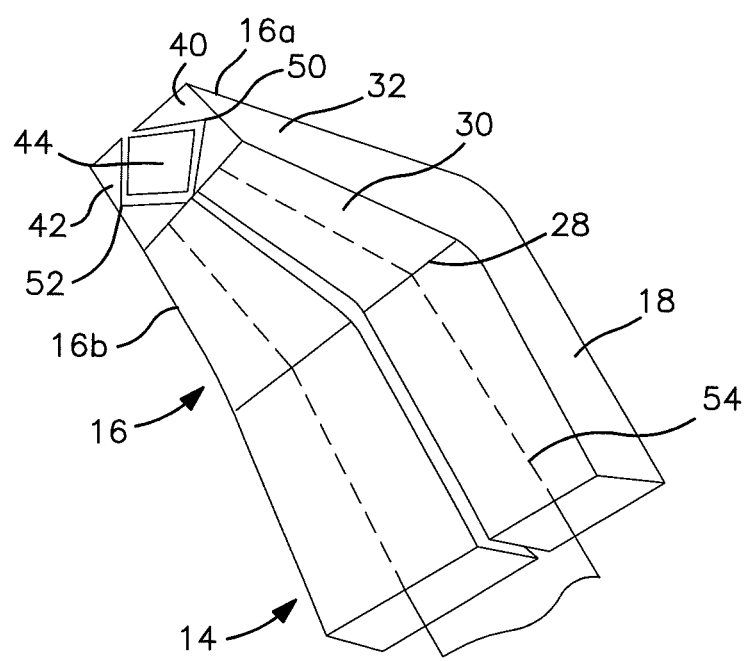
FIG. 4 is a schematic oblique front view of the head with the jaws closed.

With reference now to FIG. 4, the channels 50, 52 extend through the respective head portions 16a, 16b, preferably from the tip 38 to the base line 28'. The double gingival jaw 44 has a uniform cross-sectional shape throughout its length, preferably coextensive with the channels 50, 52 from the tip 38 toward the base line 28 where it is carried by (e.g., welded) to a central piece or arm 54. This rhomboidal shape of the gingival jaw 44 is a key feature, because it supplants the need for two pairs of pliers. The arm 54 can be pivoted either outside or between the box joint.

Figure 5A:
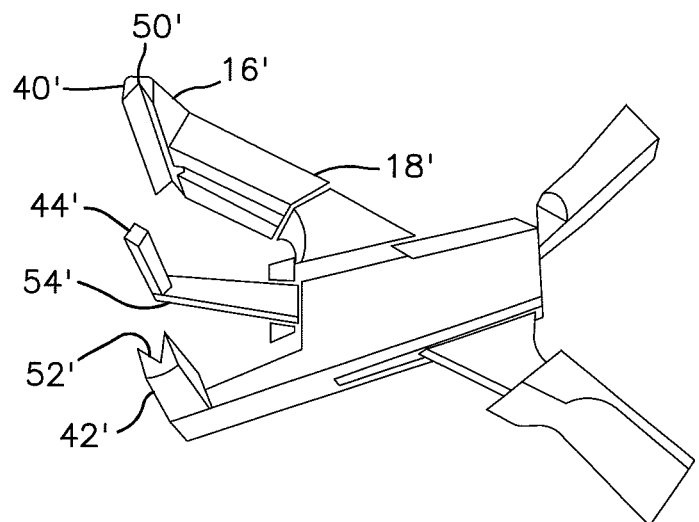
FIGS. 5A and 5B are schematic front and back view of the open jaws of an embodiment in which the arm carrying the double gingival jaw member is centrally pivoted within head portions of the occlusal jaws.
Figure 5B:
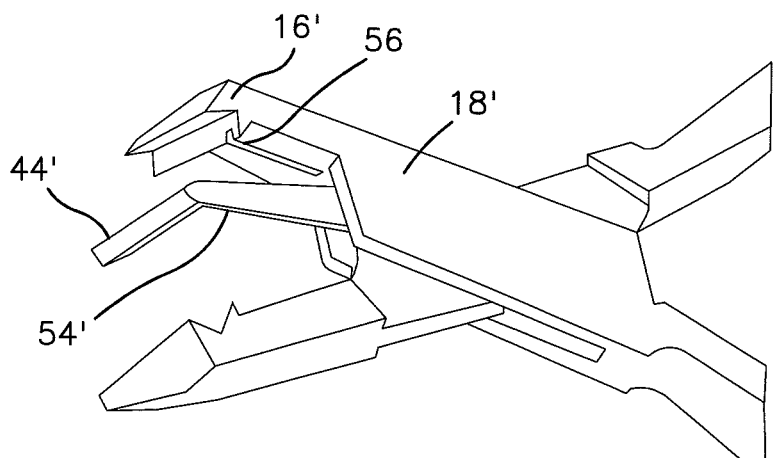
Figure 6:
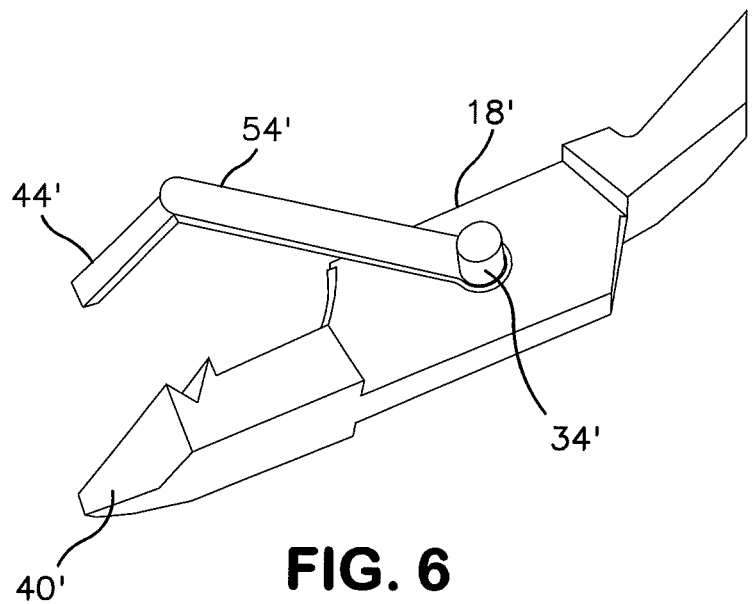
FIG. 6 is a schematic showing another view of the embodiment of FIG. 5, in which the central arm which carries the double gingival jaw, shares the same pivot as head portions of the occlusal jaws.

FIGS. 1-4 show the head 16 projecting at an obtuse angle $\alpha_2$ from the body 18, but this is not absolutely necessary. In the embodiment of FIGS. 5 and 6, each head portion 16' is aligned as an extension of the body portion 18', with the first and second jaws 40', 42' extending in parallel to pivot axis at 34. The central arm or piece 54' moves freely around the pivot 34 located inside the joint box and extends longitudinally between and in parallel with the body portions 18'. Each of the head portions 16' can have a slot 56 for receiving the arm 54' when the pliers are closed. The double gingival jaw member 44' also extends in parallel with the pivot axis 34 and the channels 50', 52' of the occlusal jaws 40', 42'.

Figure 10:
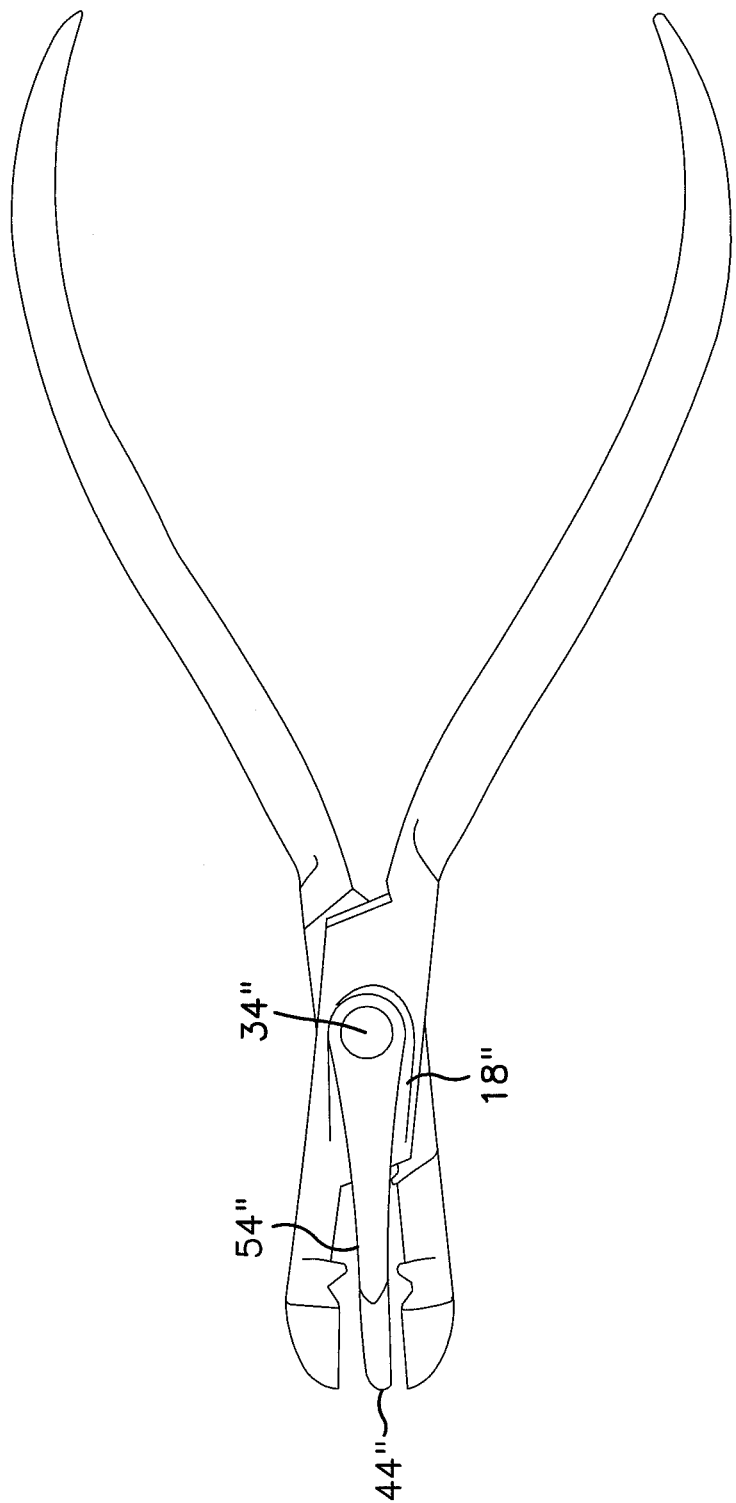
FIG. 10 shows implementing details for another embodiment of the schematic of FIG. 1, in which the central arm with double gingival jaw is pivoted on the outside of the head of one occlusal jaw member.

FIGS. 7, 8, and 10 show implementing details closely associate with the schematics of FIGS. 1-4, in which the central arm 54 is situated outside the box joint. The central arm 54" with double gingival jaw 44" is pivoted 34" on the outside of the body 18", instead of between the heads of both jaw members.

Figure 7A:
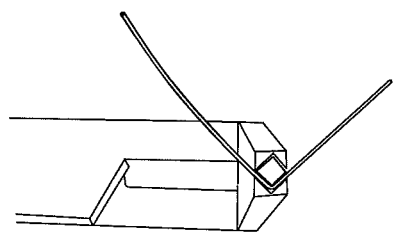
FIGS. 7A and 7B are schematics associated with FIGS. 1-4, showing opposing V-bends on upper and lower arch wires in the upper and lower mouth quadrants in the right side.
Figure 7B:
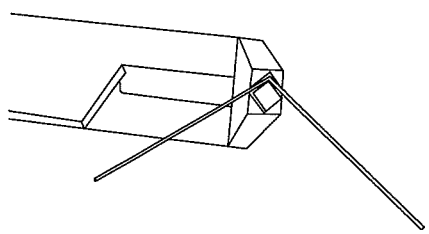

In any embodiment, one pair of pliers instantly bends super elastic arch wires in all four quadrants of a patient's mouth. Orthodontists can access arch wires from right buccal sulcus to place an intrusive V-bend on tied arch wire in the upper right quadrant of a patient's mouth, by placing the wire between the lower occlusal and gingival jaw and squeezing the pliers (FIG. 7A). For making an intrusive bend on wire in the lower right quadrant, the orthodontist can place the wire between upper occlusal jaw and gingival jaw and squeeze (FIG. 7B). The orthodontist can then invert the same pliers' positions in the left side quadrants. It can be appreciated that with no intervening wire and the handles closed, the upper and lower jaws simultaneously mate with the gingival jaws, whereas with a wire present in the active upper or lower jaw, the inactive lower or upper jaw provides solid support to the active jaw to apply bending force.

Similarly, the same pair of pliers can gain access to place V-bends on arch wires on upper and lower left quadrants, through the left buccal sulcus. For making an intrusive V-bend on the upper left quadrant, the orthodontist can place the wire between the lower occlusal jaw and gingival jaw (FIG. 8A), before squeezing fully. On the other hand, for making an intrusive V- bend on lower arch wire in the lower left quadrant, the orthodontist can place the wire between the upper occlusal jaw and gingival jaw (FIG. 8B), before squeezing fully.

The pivoted mounting of the central arm 54', 54" permits the free movement of the gingival jaw 44', 44" toward either occlusal jaw 40', 40" or 42', 42" (respectively) when the pliers are open, such that the orthodontist can shift the gingival jaw to make room for capturing the wire between the gingival jaw and either of the upper or lower occlusal jaws.

Although the resulting V-bend from full squeeze of the wire is initially at 80 degrees according to the occlusal and gingival jaw angles, the resulting V-bend remaining on the wires is about 100 degrees because of the spring back property of super elastic wires. This remaining bend angle (100 degrees) is permanent, thus creating a consistent force delivery that keeps the wires active for over a longer range and time of activation.

FIGS. 9A-9C show non-limiting examples of permanent activation bends that can be placed on super elastic titanium and nickel titanium wires extra-orally and intraorally

The invention claimed is:

1. A pair of orthodontic pliers for bending orthodontic arch wires, comprising:
    first and second elongated actuating members, each actuating member including a handle portion for grasping in the hand, and a head portion comprising a body portion extending from the handle, the actuating members being pivotally joined at their respective body portions so that the head portions can be moved toward and away from each other into respective closed and open positions;
    a first, upper occlusal jaw and a second, lower occlusal jaw formed at respective tips of the head portions of the actuating members where the first and second occlusal jaws project at an obtuse angle from the body portion, and have an internally angled V-shaped channel extending longitudinally along each occlusal jaw in a direction transverse to the body portion, where each of the V-shaped channels defines an angle of about 80 degrees and the channels are arranged to face one another;
    a central support arm pivotally coupled to both body portions and positioned between the head portions such that the central support arm lies parallel to and in the same operating plane of the handle portions;
    a gingival jaw member of rhomboidal shape projecting from an upper surface of the central support arm at the same obtuse angle as the occlusal jaws, the gingival jaw member having upper and lower externally angled corners forming angles of about 80 degrees, where the corners are adapted to mate with the internally angled V-shaped channels of the upper and lower occlusal jaws, respectively, when the head portions are in the closed position, where the central arm and the gingival jaw member pivot freely toward and away from the occlusal laws to accommodate an orthodontic arch wire therebetween for bending;
    wherein the pliers are capable of intraorally bending arch wires in all quadrants of the mouth due to the complementary configurations of the gingival law and occlusal jaws.

2. The orthodontic pliers of claim 1, wherein the first and second occlusal jaws project at an obtuse angle of at least about 135 degrees and taper in a direction from the body portion toward a tip extremity of the jaws.

3. The orthodontic pliers of claim 1, wherein each jaw projects at an obtuse angle of at least about 110 degrees.

* * * * *